United States Patent
Nessler et al.

(10) Patent No.: US 8,986,295 B2
(45) Date of Patent: Mar. 24, 2015

(54) PLANAR ELECTRODE

(75) Inventors: Norbert Nessler, Innsbruck (AT); Stephan Erbse, Rum (AT)

(73) Assignee: Nessler Medizintechnik GmbH (AT)

(*) Notice: Subject to any disclaimer, the term of this patent is extended or adjusted under 35 U.S.C. 154(b) by 2000 days.

(21) Appl. No.: 12/515,042

(22) PCT Filed: Feb. 16, 2006

(86) PCT No.: PCT/AT2006/000057
§ 371 (c)(1),
(2), (4) Date: May 15, 2009

(87) PCT Pub. No.: WO2006/089319
PCT Pub. Date: Aug. 31, 2006

(65) Prior Publication Data
US 2010/0036377 A1 Feb. 11, 2010

(30) Foreign Application Priority Data
Feb. 23, 2005 (AT) .................. A 306/2005

(51) Int. Cl.
A61B 18/16 (2006.01)
A61N 1/06 (2006.01)

(52) U.S. Cl.
CPC .. *A61B 18/16* (2013.01); *A61N 1/06* (2013.01)
USPC ................. 606/32; 600/372; 606/35

(58) Field of Classification Search
CPC ............ A61B 18/16; A61B 2018/00178; A61B 2018/165; A61B 2018/167
USPC ............ 600/372, 382–384, 391, 392; 606/35, 606/32
See application file for complete search history.

(56) References Cited

U.S. PATENT DOCUMENTS

2006/0074411 A1* 4/2006 Carmel et al. .................. 606/32

* cited by examiner

*Primary Examiner* — Michael Peffley
*Assistant Examiner* — Thomas Giuliani (57) ABSTRACT

Herein is disclosed a planar electrode which includes two equally sized electrode surfaces. The equally sized electrode surfaces are electrically separated along a linear insulation zone and adjoin directly along an inner edge portion. The two equally sized electrode surfaces include, respectively, a band-shaped extension section, which encloses the other electrode surface along its outer edge portion and thereby is separated by the extended insulation zone from the respectively enclosed electrode surface.

15 Claims, 7 Drawing Sheets

PLANAR ELECTRODE

The invention relates to a planar electrode, in particular, to a neutral electrode, for medical purposes with two electrode surfaces, electrically separated along a linear insulation zone.

Planar electrodes according to the invention are understood as all medical electrodes for attachment on the skin.

As known from DE 42 31 236 C2, a partial detachment of the neutral electrode from the skin of the patient may occur during the electrosurgical treatment and, due to the resulting strong increase of the current density, severe burns may occur in the tissue, whose effects on the patient are only noticed after recovery from the anesthesia.

In order to ensure that the contact covers the entire surface of the neutral electrode, monitoring devices have been developed which carry out resistance or symmetry measurements during the operation or between the individual treatment steps.

Therefore, the high frequency generators being employed generally have a Contact Quality Monitoring (CQM) device which verifies the correct and complete area application of the neutral electrode on the skin of the patient independent of the cutting current of the surgical apparatus. The requirement for this are two-part or multipart neutral electrodes which enable a measurement of impedance between the electrode parts. Since the skin resistance strongly varies from patient to patient, a definite statement is often very difficult of whether or not the neutral electrode rest on correctly, and thereby incorrect measurements may occur.

Through suitable measures as, for example, a linear insulation zone which is as long as possible between the electrode parts, as it is described in the DE 42 31 236 C2, the sensitivity of the impedance monitoring may be increased. In order to be able to detect also a distal detachment of the electrode, the linear insulation zone is guided in a meandering manner over the entire electrode surface. A planar detachment of the electrode has therefore an approximately proportional effect in the impedance measured by the CQM device.

Furthermore, several high frequency generators have a symmetry test circuit which determines via a measurement of the leakage current of the electrode parts whether a symmetrical current distribution is present or whether an electrode part carries a higher current portion. Such a symmetrical current distribution through the neutral electrode may be supported by the means of a suitable design of the neutral electrode. As it has been shown, it is simply not sufficient, as with the electrode according to DE 42 31 236 C2, to dimension the electrode parts with the same area since the current consumption per area unit of the electrode is strongly dependent on the orientation with respect to the operating field and also on the orientation of the surrounding muscle tissue, which is known to the specialized staff.

The purpose of the invention is therefore to provide a planar electrode as mentioned at the beginning with which, in addition to a CQM proportionalization, it is also realized to achieve symmetrical leakage currents in the application operation.

This is achieved according to the invention in that the two electrode surfaces separated by the linear insulation zone are at least partly enclosed by band-shaped extension sections of the other electrode surface.

In this way, a long insulation path may be achieved by the electrode according to the invention, which enables a high sensitivity of the CQM measurement, as well as an electrode surface design may be selected which guarantees a reliable symmetry measurement of the leakage currents during the operation since also in the edge regions, which have an disproportional influence on the measurement results, the portions of the electrode surface may be arranged having the same size.

A further embodiment of the invention may consist in that the two electrode surfaces adjoin each other on a side along an inner part of the linear insulation zone, that the two electrode surfaces comprise, respectively, a band-shaped extension section, and that the band-shaped extension sections of the two electrode surfaces are guided along the outer parts going out from the inner part of the linear insulation zone around the other electrode surface.

The two centrally located electrode surfaces are thereby enclosed by the band-shaped extension sections of the respective other electrode surface. A relatively long insulation path and also a surface distribution of the electrode surfaces being symmetric compared with the edge regions are thereby possible.

A simple constructive design results when the inner part of the linear insulation zone runs linearly and extends along a secondary axis of the planar electrode.

In order to prevent the formation of strong local current densities during the application, rounded electrode forms which avoid smaller radii of curvature in the edge regions are advantageous. According to a development of the invention, the two electrode surfaces may be formed therefore semicircular at their end opposite to the inner part, which end of the extension sections is enclosed by the outer parts of the linear insulation zone in a crescent-shaped manner.

A high surface symmetry of the individual electrode is advantageous for the application with symmetry current measurements. In respect thereof, a feature of the electrode according to the invention may consist in that the two electrode surfaces are formed double symmetrically around an axis perpendicular to the plane of the planar electrode.

Further, terminal lugs may be arranged at an end of one of the extension sections of the planar electrodes and at a transition region between the other one of the planar electrodes and the other extension section. In this way, connecting the electrode according to the invention may take place at one side, whereby the side opposite to this side which does not have any terminals, is suitable to be oriented on the patient in the direction of the operating field.

An advantageous symmetrical arrangement may be achieved when the terminal lugs extend on one side of the planar electrode in the imaginary extension of the inner part along the secondary axis.

Further, it has proven to be favourable for mechanical reasons and symmetrical reasons, when the band-shaped extension sections extend, respectively, in a corner region situated along the secondary axis of the planar electrode, away from these, wherein the corner regions are equally spaced with respect to a main axis of the planar electrode, and that the extension sections extend, respectively, around the other one of the two electrode surfaces up to substantially the vicinity of the corner region of the other electrode surface.

Another embodiment of the invention, in which an increased length of the insulation zone is present, may consist in that a projection of the band-shaped extension sections extends, respectively, along the main axis into the respective other electrode surface.

In the central region of the electrode according to the invention, the current density is relatively low during the application so that this zone may be used to provide terminals for the electrode surfaces. This may be achieved by providing terminal lugs in the middle region which are connected with the electrode surfaces.

This attachment of the terminal lugs in the central region of a planar electrode, in particular, a neutral electrode, may also be used for all known embodiments of this type of electrode and is claimed as a separate invention.

A multiplication of the inventive principle which lies within the scope of protection of the invention may be achieved for example in that the extension sections guided around the respective other electrode surface are subsequently guided back into the region of the associated electrode surface and there, separated by the linear insulation zone, enclose the other extension sections.

In this regard, other forms of guiding the extension sections are feasible within the framework of the invention. Thus, it may be provided that the band-shaped extension sections are guided around the two electrode surfaces intertwining in spiral form two or several times.

With the concentric arrangement of the terminal lugs, when these are connected therefore directly with the two centrally arranged electrodes, it may be advantageous when the current part of the inner region is influenced compared to that of the outer region such that the current concentration otherwise present in the edge regions of the electrode distributes itself more evenly over the entire electrode surface. This may be realized, for example, by providing an impedance gradient directed from outside to inside, that means, the further the current flows into the outer region of the electrode, the impedance for it increases.

According to an embodiment of the invention, along the course of the band-shaped extension sections, the band-shaped extension sections may be interrupted for this purpose at one or at a plurality of positions and impedances may be interposed for forming an impedance gradient.

In the following, the invention will be explained in detail on the basis of the exemplary embodiments shown in the drawings.

Figure 1:
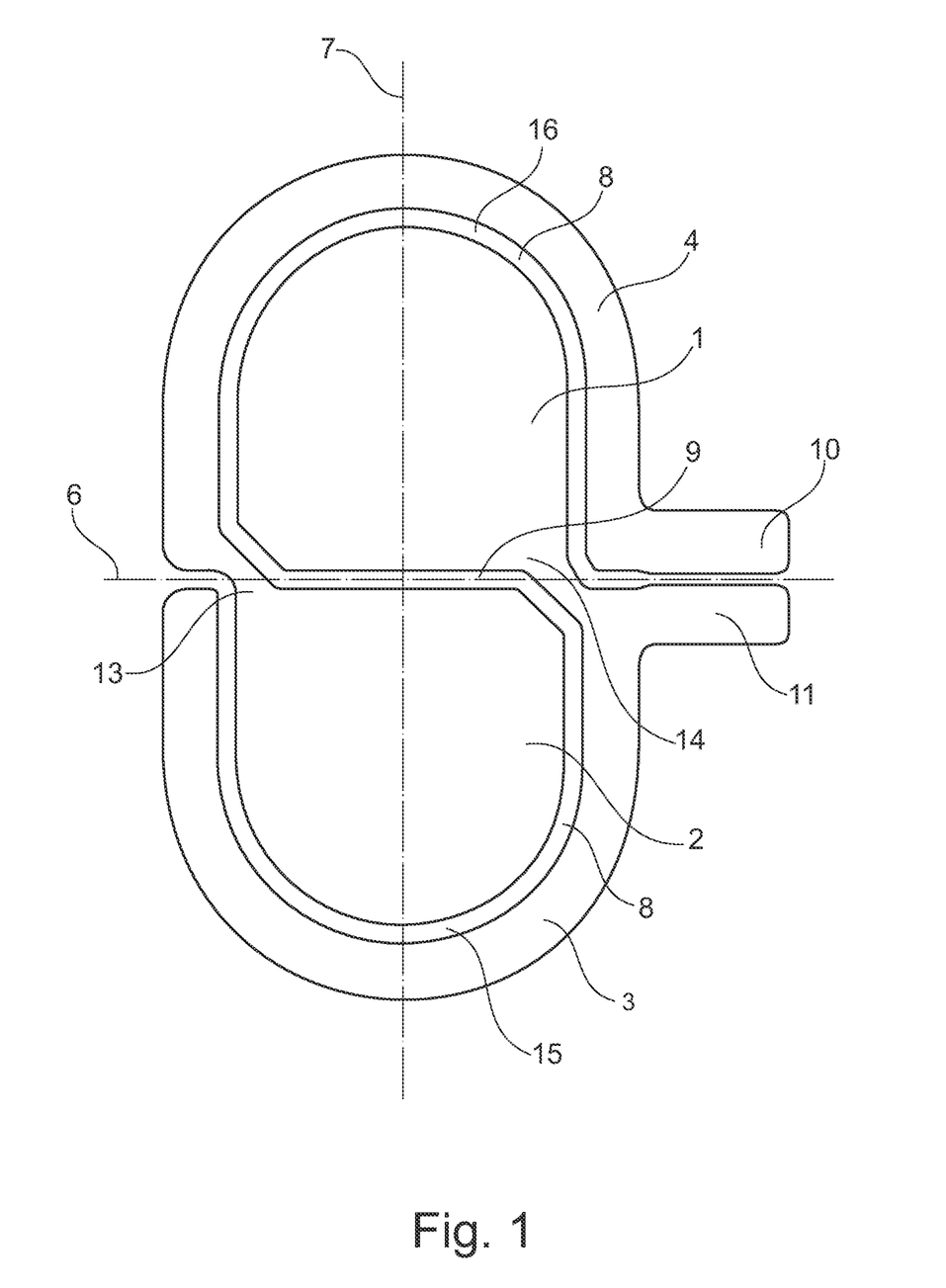
FIG. 1 shows a schematic top view of an embodiment of the electrode according to the invention.

In the drawings:

FIG. 1 shows a planar electrode, in particular, a neutral electrode for high frequency surgery. The two surfaces encircled by the solid lines are two electrode surfaces 1, 2, which are electrically separated from each other along a linear insulation zone 8.

The planar electrode shown in the form of an exemplary embodiment may be implemented in any of the known materials for fabricating neutral electrodes for single or multiple uses. In particular, the conductive surface may consist of a metal foil coated with a conductive gel or adhesive. The linear insulation zone 8 is, for example, 2 to 5 mm wide and may be either completely free of conductive material or be also covered with weak transverse conductive gel or adhesive. Design forms deviating from these details may also be used as a planar electrode within the framework of the invention.

According to the invention, the two electrode surfaces 1, 2 are separated from each other by the linear insulation zone 8, at least partly enclosed by band-shaped extension sections 3, 4 of the other electrode surface. Opposite the band-shaped extension sections 3, 4 which are arranged on the outside, the two electrode surfaces 1, 2 take up a central inner region of the electrode according to the invention.

The band-shaped extension sections 3, 4 are formed narrow in comparison to the centrally arranged electrode surfaces 1, 2, that is, their length is clearly greater than their width.

In the inner region the two electrode surfaces 1, 2 adjoin on a side along an inner part 9 of the linear insulation zone 8, and the two electrode surfaces 1, 2 comprise, respectively, a band-shaped extension section 3, 4, which extends, respectively, around the other electrode surface.

The band-shaped extension sections 3, 4 of the two electrode surfaces 1, 2 are guided along the outer parts 15, 16 going out from the inner part 9 of the linear insulation zone 8 around the respective other electrode surface.

For further geometric considerations, a main axis 7 and a secondary axis 6 of the electrode according to the invention are indicated in FIG. 1.

The inner part of the linear insulation zone 8 proceeds linearly and extends along a secondary axis 6 of the planar electrode.

At their ends opposite the inner part 9, the electrode surfaces 1, 2 are formed semicircular. These ends are enclosed by the extension sections 3, 4 through the outer parts 15, 16 of the linear insulation zone 8, respectively, in crescent-shaped manner.

In the exemplary embodiment shown in FIG. 1, the electrode according to the invention comprises an oval form. The invention, however, is not limited to this form; it may also be realized in another geometric form. It may be realized, for instance, arbitrarily compressed or stretched compared to the construction form represented in FIG. 1, therefore, may be from transversely divided via round to longitudinally divided. Furthermore, the space of the linear insulation zone 8 from the edge may be broadly varied.

The two electrode surfaces 1, 2 are substantially formed double symmetrically around an axis perpendicular to the plane of the electrode according to the invention which runs through the intersection of the main and secondary axes 7, 6. The type of symmetry may be also otherwise configured.

For the removal of the leakage current, respectively, for the implantation of a measurement current, terminal lugs 10, 11 are arranged at an end of one of the extension sections 3, 4 of the planar electrodes 1, 2 and at a transition region between the other one of the planar electrodes 1, 2 and the other extension section 3, 4. The terminal lugs 10, 11 extend thereby on a side of the planar electrode in the imaginary extension of the inner part 9 along the secondary axis 6.

As further shown in FIG. 1, the extension sections 3, 4 extend in a corner region 13, 14 situated along the secondary axis 6 of the planar electrodes 1, 2, respectively, away from these, wherein the corner regions 13, 14 are equally spaced opposite to the main axis 7 of the planar electrode. The band-shaped extension sections 3, 4 extend, respectively, around the other one of the two electrode surfaces 1, 2 up to substantially the vicinity of the corner region 13, 14 of the other electrode surface.

Figure 2:
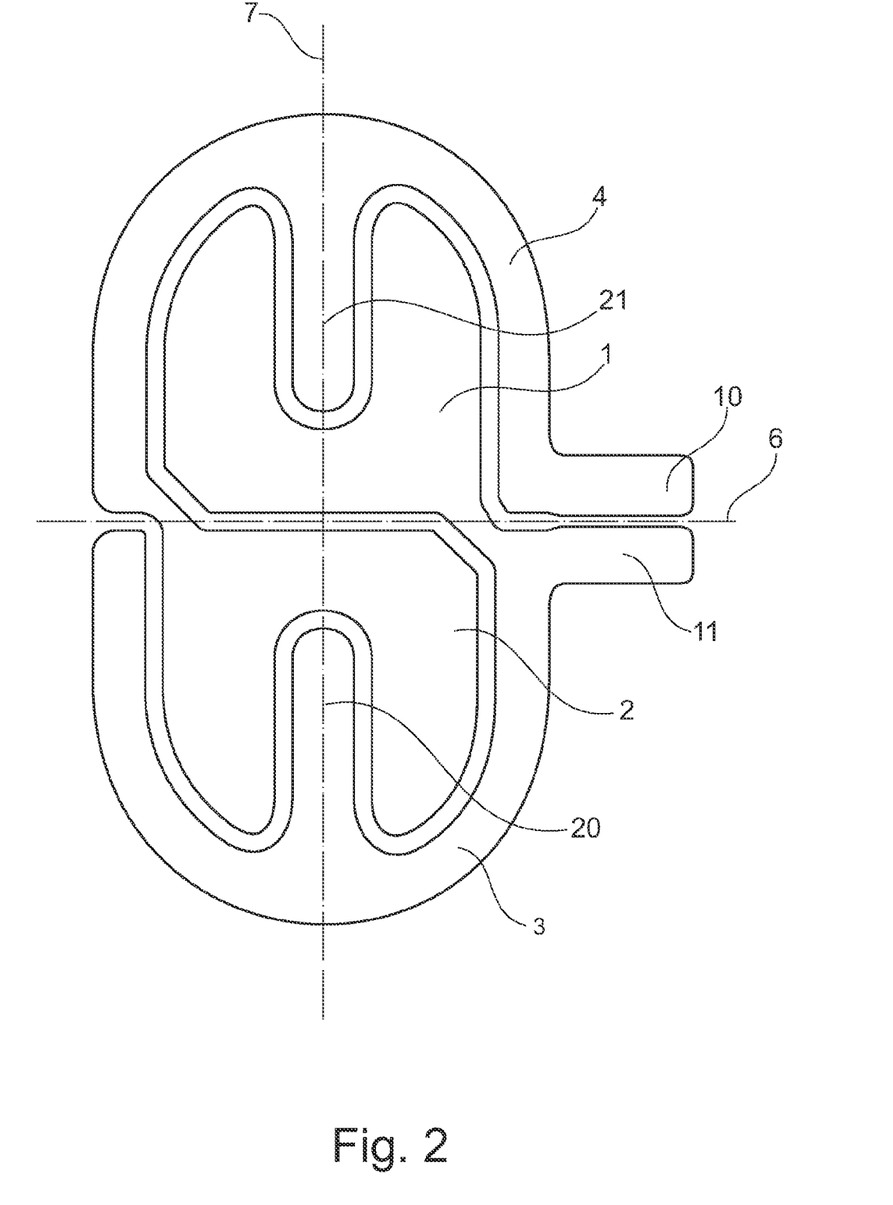
FIG. 2 shows a schematic top view of another embodiment of the electrode according to the invention.

By the embodiment shown in FIG. 2, a projection 20, 21 of the band-shaped extension sections 3, 4 extends, respectively, along the main axis 7 into the respective other electrode surface 1, 2 and lengthens thereby the linear insulation zone 8.

Figure 3:
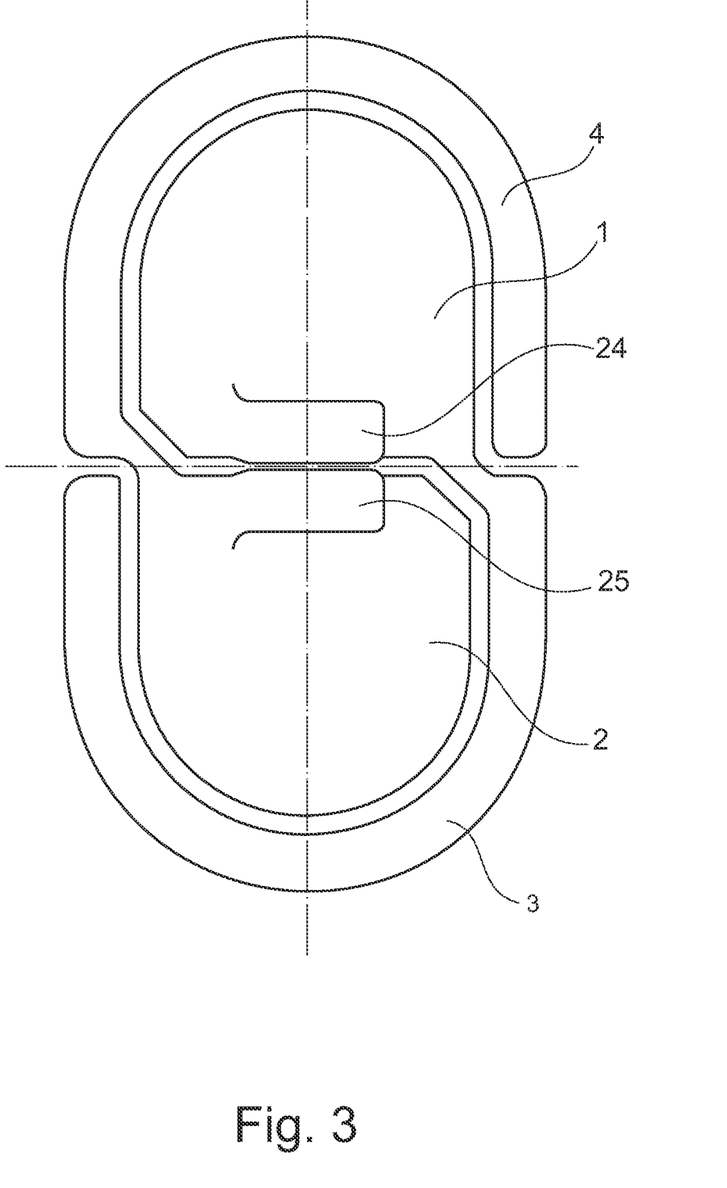
FIG. 3 shows a schematic top view of another embodiment of the electrode according to the invention.

The middle region of the electrode according to the invention absorbs a comparatively low current portion due to the edge effect and has, therefore, a lower degree of efficiency than the edge regions. In the embodiment shown in FIG. 3, space-saving and material-saving terminal lugs 24, 25 are therefore provided in this middle region, which are coupled with the electrode surfaces 1, 2.

Figure 4:
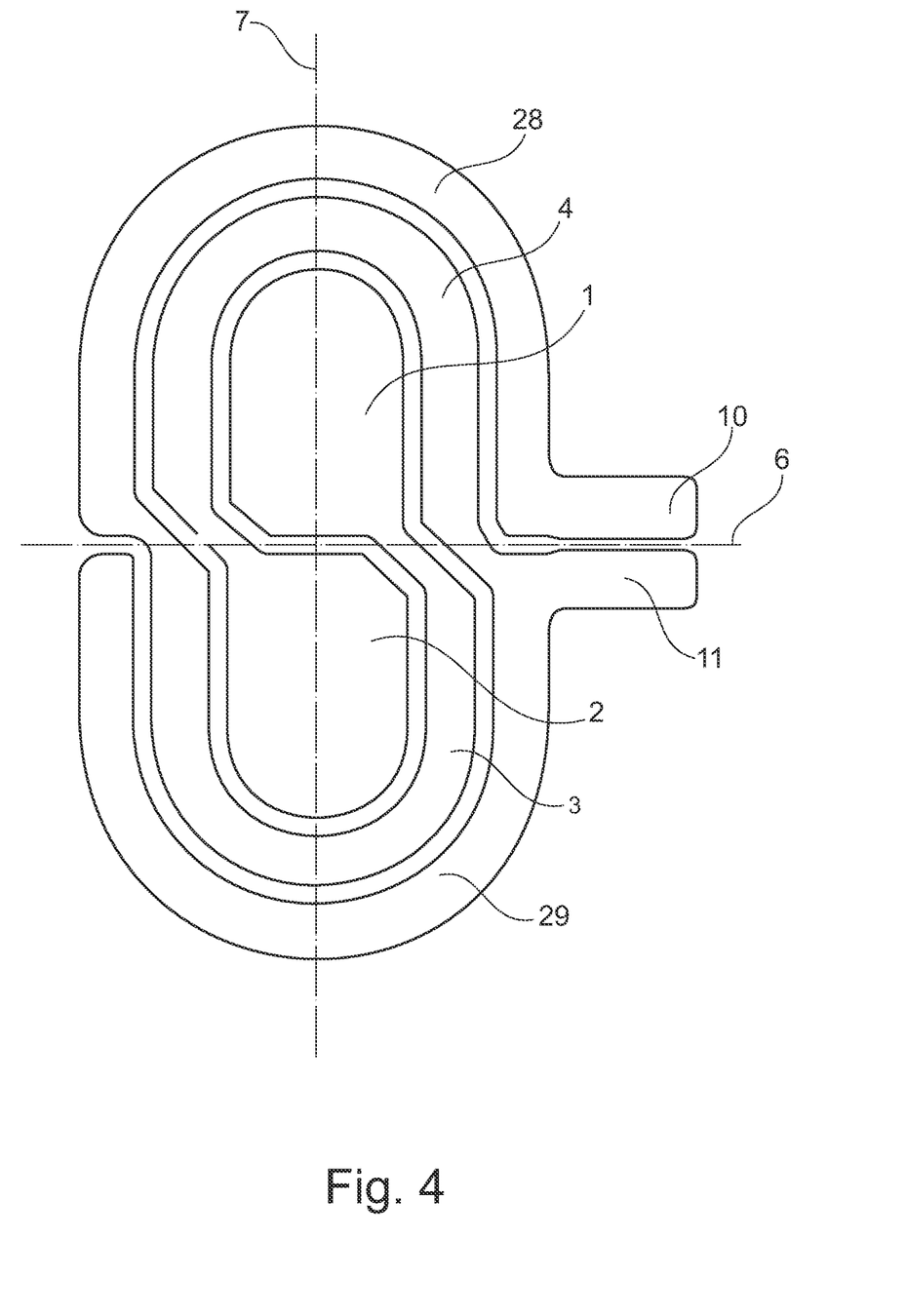
FIG. 4 shows a schematic top view of another embodiment of the electrode according to the invention.

Finally, in the embodiment shown in FIG. 4 of the electrode according to the invention, the extension sections 3, 4 guided around the respective other electrode surface 1, 2 subsequently are guided back in the region of the associated electrode surface and enclose the other extension sections 3, 4 in form of other exterior sections 28, 29.

Figure 5:
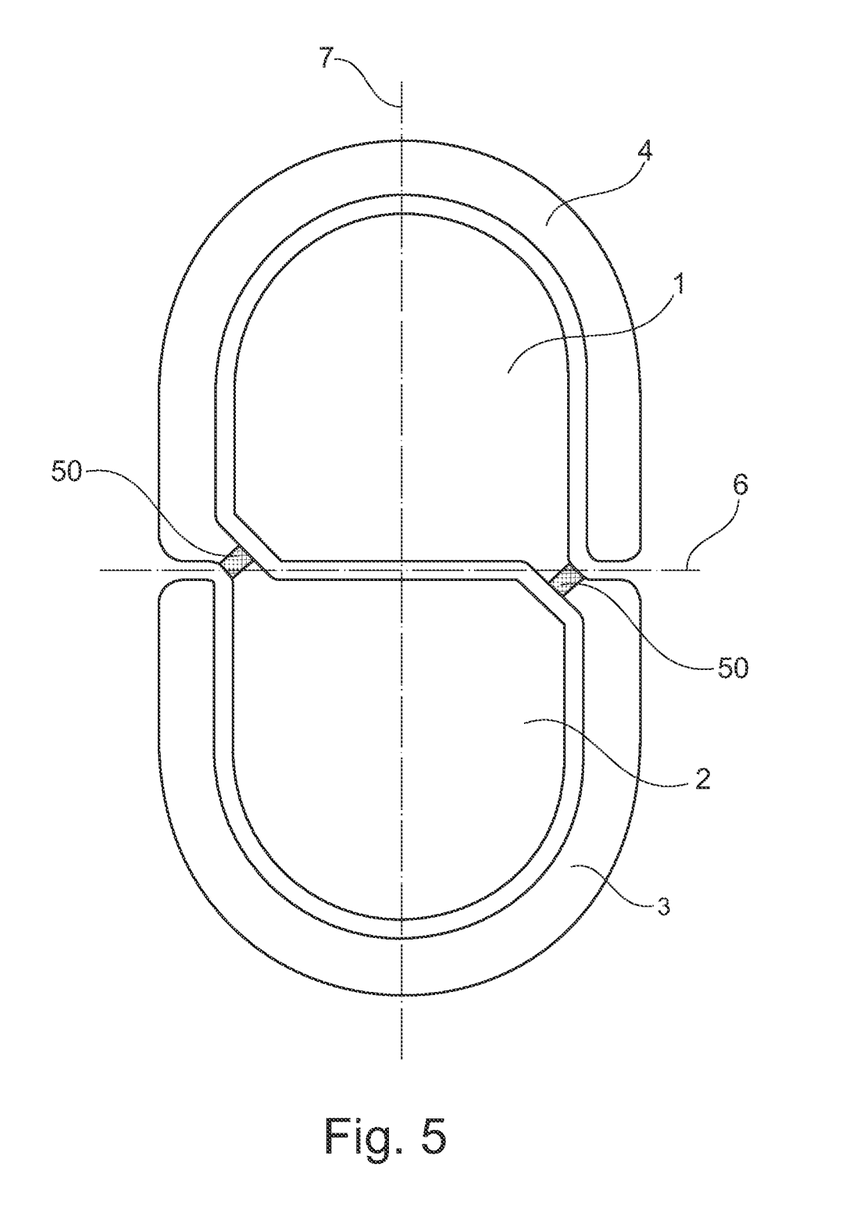
FIG. 5 shows a schematic top view of another embodiment of the electrode according to the invention and FIG. 6 shows a schematic top view of another embodiment of the electrode according to the invention.
Figure 6:
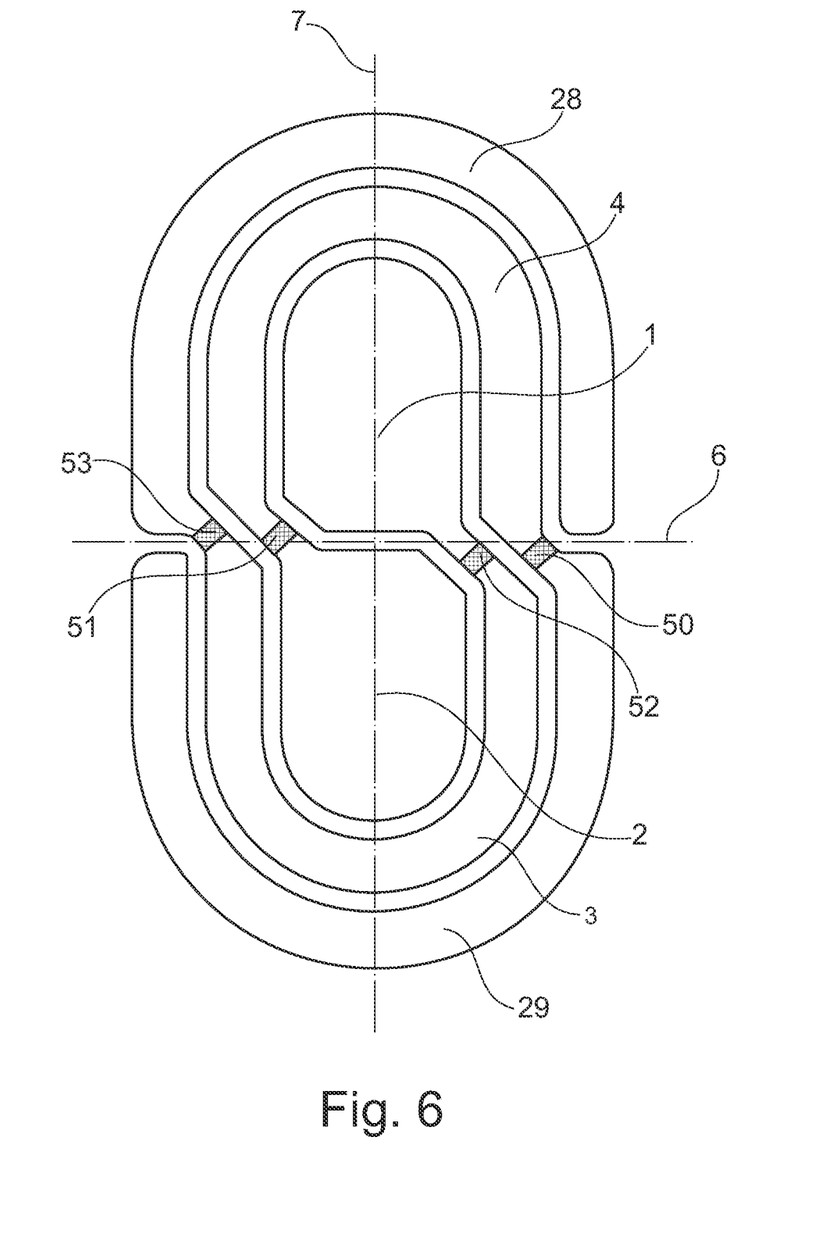
Figure 7:
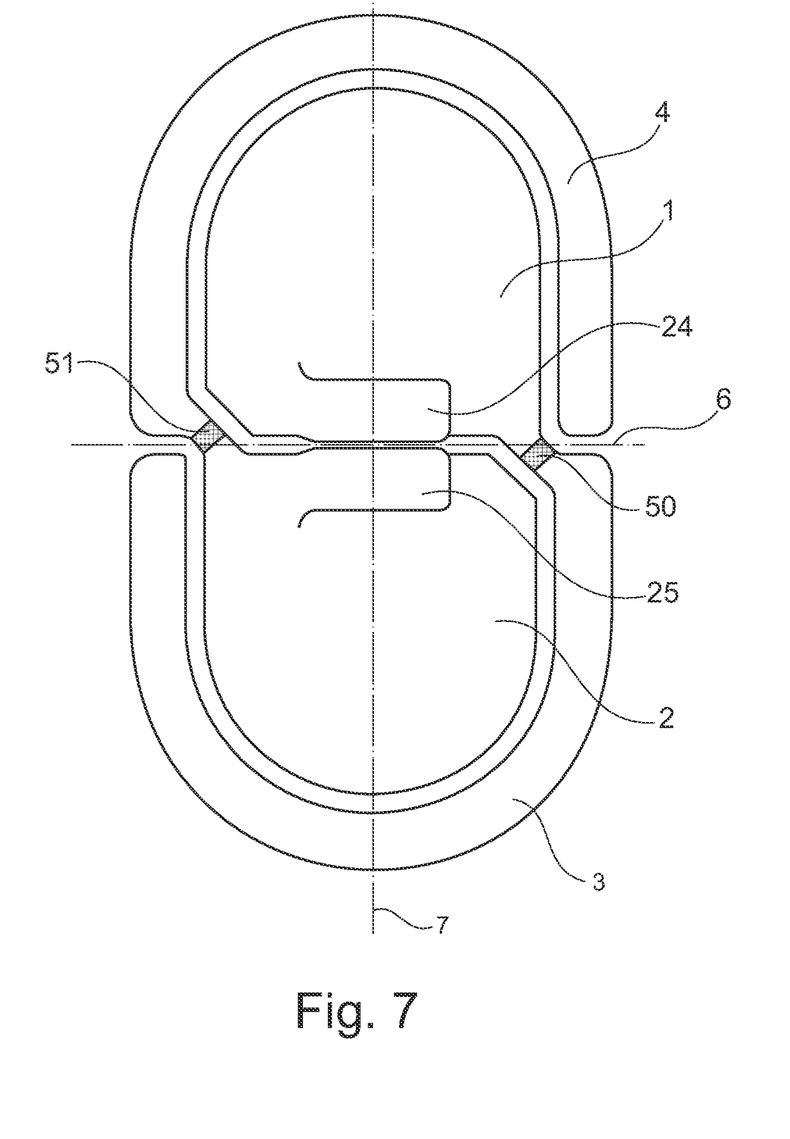

FIGS. 5, 6 and 7 show further exemplary embodiments of the invention in which the terminal lugs 24, 25 (FIG. 7) are arranged concentrically. In the FIGS. 5 and 6, the attachment of the terminal lugs is not shown because it may occur in a manner other than the one shown in FIG. 7, however, this does not contribute anything to the invention.

In the electrodes according to FIGS. 5, 6, and 7, the band-shaped extension sections 3, 4 are interrupted at one or at a plurality of positions along their course and impedances 50, 51, 52, 53 are interposed for forming an impedance gradient. The arrangement of impedances may take place, for example, such that the secondary axis 6 runs through the attachment positions of the impedances 50, 51, 52, 53, whereby a gradual increase of the impedance to the outside may be realized. Thereby, the current distribution within the electrode according to the invention may be influenced. The type, the dimensioning and the attachment positions of the impedances 50, 51, 52, 53 may be varied as required.

The impedances 50, 51, 52, 53 themselves as well as the electrode surfaces 1, 2 and the extension sections 3, 4, or the exterior extension sections 28, 29, respectively, may be imprinted by imprinting more or less conductive enamels.

What is claimed is:

1. A planar electrode for medical purposes comprising two equally sized electrode surfaces, electrically separated along a linear insulation zone, which electrode surfaces adjoin directly along an inner edge portion, characterized in that:
    said two equally sized electrode surfaces comprise, respectively, a bandshaped extension section, which encloses said other electrode surface along an outer edge portion and thereby is separated by said linear insulation zone from said respectively enclosed electrode surface,
    wherein said two electrode surfaces are formed approximately symmetrically around an axis perpendicular to the plane of said planar electrode,
    wherein respective terminal lugs are arranged at an end of one of said extension sections of said electrode surfaces and at a transition region between the other one of said electrode surfaces and said other extension section.

2. The planar electrode according to claim 1, characterized in that:
    an inner part of said linear insulation zone and said adjoining inner edge portions of said two equally sized electrode surfaces run linearly and extend along a secondary axis of said planar electrode.

3. The planar electrode according to claim 2, characterized in that:
    said two equally sized electrode surfaces are formed to have a semicircular shape at their end opposite to said inner part of said linear insulation zone, which end is encircled by said band-shaped extension section of other electrode surface and by an outer part of said linear insulation zone, respectively in crescent-shaped manner.

4. The planar electrode according to claim 2, characterized in that:
    said two electrode surfaces are formed double symmetrically around the axis perpendicular to the plane of said planar electrode.

5. The planar electrode according to claim 1, characterized in that:
    an inner part of said linear insulation zone and said adjoining inner edge portions of said two equally sized electrode surfaces run linearly, and said two equally sized electrode surfaces are formed to have a semicircular shape at their end opposite to said inner part of said linear insulation zone, which end is encircled by said band-shaped extension section of other electrode surface and by an outer part of said linear insulation zone, respectively in crescent-shaped manner.

6. The planar electrode according to claim 5, characterized in that:
    said two electrode surfaces are formed double symmetrically around the axis perpendicular to the plane of said planar electrode.

7. The planar electrode according to claim 1, characterized in that:
    said two electrode surfaces are formed double symmetrically around the axis perpendicular to the plane of said planar electrode.

8. The planar electrode according to claim 1, characterized in that:
    said terminal lugs comprise extensions extending at one side of the planar electrode, wherein the extensions of the terminal lugs are in a direction of a fictional extension of an inner part of said linear insulation zone, along a secondary axis of said planar electrode.

9. The planar electrode according to claim 1, characterized in that:
    said extension sections respectively project in a corner region situated along a secondary axis of said planar electrode, wherein the corner regions are equally spaced to a main axis of said planar electrode, and said extension sections extend, respectively, around the other one of said two electrode surfaces up to substantially the vicinity of said corner region of the other electrode surface.

10. The planar electrode according to claim 1, characterized in that:
    a projection of each of said band-shaped extension sections extends, respectively, along a main axis of said planar electrode around the respective other electrode surface.

11. The planar electrode according to claim 1, characterized in that:
    said terminal lugs are provided in a middle region of said planar electrode, wherein said terminal lugs are connected with said electrode surfaces.

12. The planar electrode according to claim 1, characterized in that:
    respectively one of said extension sections is guided around said respective other electrode surface and each of the extension sections is subsequently guided back into a region of its associated electrode surface, and there, separated from the extension section associated with the respective other electrode surface by said linear insulation zone, encircles the other extension section.

13. The planar electrode according to claim 1, characterized in that:
    said band-shaped extension sections are guided around said two electrode surfaces, intertwining in spiral form two or several times.

14. The planar electrode according to claim 1, characterized in that:
    along the course of said band-shaped extension sections, each of the extension sections is sectioned by impedances at one or at a plurality of positions, wherein said impedances are interposed for forming an impedance gradient.

15. The planar electrode according to claim 14, characterized in that:
an inner part of said linear insulation zone and said adjoining inner edge portions of said two equally sized electrode surfaces run linearly and extend along a secondary axis of said planar electrode, and said secondary axis extends through attachment positions of said impedances.

* * * * *